(12) United States Patent
Kampas et al.

(10) Patent No.: US 8,876,912 B2
(45) Date of Patent: Nov. 4, 2014

(54) METHOD AND DEVICE FOR CONTROLLING AN ARTIFICIAL ORTHOTIC OR PROSTHETIC JOINT

(75) Inventors: Philipp Kampas, Vienna (AT); Martin Seyr, Vienna (AT); Roland Pawlik, Vienna (AT); Sven Kaltenborn, Duderstadt (DE)

(73) Assignee: Otto Bock Healthcare Products GmbH, Vienna (AT)

( * ) Notice: Subject to any disclaimer, the term of this patent is extended or adjusted under 35 U.S.C. 154(b) by 153 days.

(21) Appl. No.: 13/509,234

(22) PCT Filed: Nov. 12, 2010

(86) PCT No.: PCT/EP2010/006891
§ 371 (c)(1),
(2), (4) Date: May 10, 2012

(87) PCT Pub. No.: WO2011/057790
PCT Pub. Date: May 19, 2011

(65) Prior Publication Data
US 2012/0232673 A1    Sep. 13, 2012

(30) Foreign Application Priority Data
Nov. 13, 2009  (DE) .................. 10 2009 052 888

(51) Int. Cl.
*A61F 2/64* (2006.01)
*A61F 2/70* (2006.01)
*A61F 2/68* (2006.01)
*A61F 5/01* (2006.01)
*A61F 2/76* (2006.01)
*A61F 2/50* (2006.01)

(52) U.S. Cl.
CPC .......... *A61F 2/68* (2013.01); *A61F 2002/7635* (2013.01); *A61F 5/0125* (2013.01); *A61F 2002/7625* (2013.01); *A61F 2002/704* (2013.01); *A61F 2005/0169* (2013.01); *A61F 2/70* (2013.01); *A61F 2/64* (2013.01); *A61F 2/76* (2013.01); *A61F 2002/5003* (2013.01); *A61F 2002/5033* (2013.01); *A61F 2002/6818* (2013.01)
USPC ............................................. 623/24; 623/44

(58) Field of Classification Search
None
See application file for complete search history.

(56) References Cited

U.S. PATENT DOCUMENTS 6,755,870 B1   6/2004   Biedermann et al.
7,731,759 B2   6/2010   Pusch et al.
(Continued)

FOREIGN PATENT DOCUMENTS

DE   19859931 A1   7/2000
DE   60309685 T2   9/2007
(Continued)

OTHER PUBLICATIONS

PCT International Search Report for International Patent Application No. PCT/EP2010/006891, mailed Mar. 17, 2011.

*Primary Examiner* — David H Willse
(74) *Attorney, Agent, or Firm* — Holland & Hart

(57) ABSTRACT

The invention relates to a device and method for controlling an artificial orthotic or prosthetic joint of a lower extremity, comprising a resistance unit with which at least one actuator is associated, via which the bending and/or stretching resistance is varied depending on sensor data. During the use of the joint, status information is provided via sensors. According to the invention, the resistance is increased in the standing phase or while standing from a starting value depending on the ground reaction force up to a locking point of the joint.

20 Claims, 5 Drawing Sheets

(56) References Cited

U.S. PATENT DOCUMENTS

| | | |
|---|---|---|
| 2007/0027555 A1 | 2/2007 | Palmer et al. |
| 2008/0228287 A1 | 9/2008 | Ninomiya |
| 2009/0030530 A1 | 1/2009 | Martin |
| 2009/0265018 A1 | 10/2009 | Goldfarb et al. |
| 2010/0305716 A1 | 12/2010 | Pusch et al. |
| 2011/0087339 A1 | 4/2011 | Pusch et al. |

FOREIGN PATENT DOCUMENTS

| | | |
|---|---|---|
| DE | 102006021802 A1 | 11/2007 |
| DE | 102007053389 A1 | 5/2009 |
| DE | 102008008284 A1 | 8/2009 |
| EP | 1570817 A1 | 9/2005 |
| EP | 1494626 B1 | 11/2006 |
| JP | 2008220636 | 9/2008 |
| RU | 2076670 C1 | 4/1997 |
| RU | 2254832 C1 | 6/2005 |

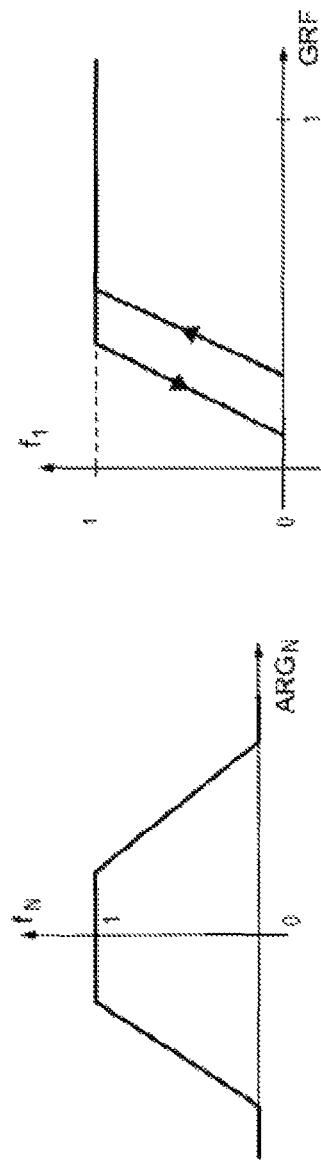
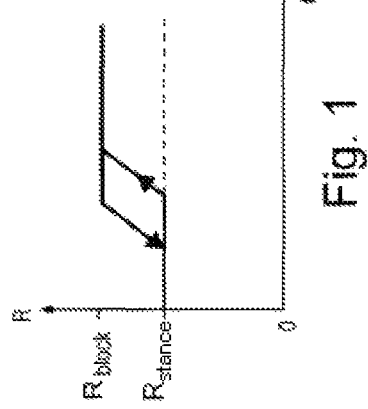

METHOD AND DEVICE FOR CONTROLLING AN ARTIFICIAL ORTHOTIC OR PROSTHETIC JOINT

TECHNICAL FIELD

The invention relates to a method and a device for controlling an orthotic or prosthetic joint of a lower extremity with a resistance device, which is assigned at least one actuator by way of which the bending and/or stretching resistance is changed in dependence on sensor data, information pertaining to the state being provided by way of sensors during the use of the joint.

BACKGROUND

Appropriate prosthetic care for geriatric patients requires that the needs of the patients, respective activities and medical necessities are addressed. The need for safety is often at the forefront, so that while standing a locking of the knee joint is desired. It is intended that the locking can as far as possible be activated both load-dependently and angle-dependently and induce the feeling of stability in every standing situation, since the coordinating capability, mobility and physical strength of such patients may sometimes be limited.

If the patient is mobile, during walking there should be a high flexion resistance in the standing phase in order to avoid unwanted bending, since bending often cannot be compensated quickly enough by a stretching from the hip.

Sitting on the other hand requires a low resistance, both in the direction of extension and in the direction of flexion, in order that the patient can move unhindered.

It may also be necessary to provide a triggering of the swing phase, in order to make walking more comfortable for the patient.

Artificial joints, in particular knee joints, for ortheses or prostheses have an upper connection part and a lower connection part, which are connected to each other by way of a joint device. In the case of a knee joint, receptacles for an upper leg stump or an upper leg rail are arranged on the upper connection part, while a lower leg shaft or a lower leg rail is arranged on the lower connection part. In the simplest case, the upper connection part and the lower connection part are connected to each other pivotably by a single-axis joint. Only in exceptional cases is such an arrangement sufficient for ensuring the desired success, for example support in the case of the use of an orthesis or a natural gait pattern in the case of use in a prosthesis.

In order to represent as naturally as possible or be conducive to the various requirements during the various phases of a step, or in the case of other tasks, resistance devices which offer a flexion resistance or an extension resistance are provided. The flexion resistance is used to set how easily the lower connection part can be pivoted with respect to the upper connection part in the direction of flexion. In the case of a knee joint, the flexion resistance is therefore used to set how easily the lower leg shaft or the lower leg rail swings backward in relation to the upper leg shaft or the upper leg rail when a force is applied. The extension resistance retards the forward movement of the lower leg shaft or the lower leg rail and may form a stretching stop. In the case of other types of joint, such as the hip joint or the ankle joint, these statements apply in a way corresponding to the kinematic conditions.

It is possible by using settable resistance devices to adapt the respective flexion resistance and extension resistance to the user of the prosthetic or orthotic device or to make allowance for different gait or movement situations, in order to be able to offer an adapted resistance under changing conditions.

DE 10 2008 008 284 A1 discloses an orthopedic knee joint with an upper part and a lower part arranged pivotably thereon and assigned a number of sensors, for example a bending angle sensor, an acceleration sensor, an inclination sensor and/or a force sensor. The extension stop is set in dependence on the sensor data determined.

DE 10 2006 021 802 A1 describes a control of a passive prosthetic knee joint with adjustable damping in the direction of flexion for the adaptation of a prosthetic device with upper connecting means and a connecting element to an artificial foot. The adaptation is for climbing stairs, a low-torque lift of the prosthetic foot being detected and the flexion damping being lowered in a lifting phase to below a level that is suitable for walking on level ground. The flexion damping may be raised in dependence on the changing of the knee angle and in dependence on the axial force acting on the lower leg.

DE 10 2007 053 389 A1 describes a method and a device for controlling an orthopedic joint of a lower extremity with at least one degree of freedom, with an adjustable actuator for adapting to walking situations that differ from walking on level ground an orthopedic device which has upper connecting means to a limb and an orthopedic joint arranged in a jointed manner distally in relation to the connecting means. In this case, a number of parameters of the orthopedic device are detected by way of sensors, the detected parameters are compared with criteria that have been produced on the basis of a number of parameters and/or parameter profiles and stored in a computer unit, and a criterion that is suitable on the basis of the parameters or parameter profiles determined is selected. On the basis of the criterion selected, bending resistances, bending extents, driving forces and/or how they vary over time are set in order to control special functions that deviate from walking on level ground. A tilting angle of part of the orthopedic device in space and/or a variation of a change in tilting angle of part of the orthopedic device may be used as parameters.

Furthermore, the prior art discloses what are known as brake knee joints, in which the flexion resistance and extension resistance are mechanically increased as axial loading becomes greater. This is achieved in the simplest case by providing two braking surfaces which are pressed onto each other by the ground reaction force. Such a configuration cannot be used on the braking device for modern prosthetic knee joints with controlled resistance devices.

It has proven successful for knee joints to offer a high resistance in the standing phase during walking or while standing, the joint not being locked completely. In the case of a fully stretched knee joint, the bending of the joint is prevented by the force vector lying ahead of the joint axis, and consequently the joint being pressed into the stretching stop. As soon as the force vector migrates behind the joint axis, there is the risk of the joint buckling. It is therefore necessary likewise to offer an increased resistance in a slightly bent position. The fact that the joint does not completely lock in a slightly bent position has the advantage that the user of the joint still has possibilities of intervening in the movement of the joint. Should he for example be standing on stairs and lose his balance, a locked joint would cause him to fall in an uncontrolled manner, whereas he can still bend a joint with a high flexion resistance by means of the stump force and thereby mitigate the consequences of falling or prevent falling entirely. Likewise, high damping when standing makes it easier for the joint to be maneuvered in confined spaces or to be set down.

If the joint only offers a high resistance and does not completely lock, it is not possible for example for loading to be applied to the prosthesis when standing on inclined surfaces if the ground reaction force vector migrates too far toward the heel, and consequently no longer lies ahead of the knee axis but behind the knee axis and thereby bends the knee. Standing on a bent knee is also not possible, because the knee bending has the effect that the knee joint axis migrates ahead of the ground reaction force vector and, as a result, the knee is bent further.

Furthermore, the prior art discloses devices in which a separate mode must be set in order to activate locked standing on a ramp or on a bent knee. In such a mode, the joint cannot be bent any further than up to a settable angle. To walk any further or sit down, it is necessary to change deliberately to another mode.

SUMMARY

The object of the present invention is to provide a method and a device with which it is possible automatically to load the knee with an increased resistance or to lock it in certain situations, without a deliberate activation or deactivation of the mode having to be performed.

This object is achieved according to the invention by a method according to the main claim and a device according to the further independent claim. Advantageous configurations and developments of the invention are presented in the dependent claims.

The method according to the invention for controlling an orthotic or prosthetic joint of a lower extremity with a resistance device, which is assigned at least one actuator by way of which the bending and/or stretching resistance is changed in dependence on sensor data, information pertaining to the state being provided by way of sensors during the use of the knee joint, provides that, in the standing phase or when standing, the resistance is increased from an initial resistance up until a locking of the joint in dependence on the measured ground reaction force. After the detection of the standing phase or of standing, in the presence of a predetermined ground reaction force the joint resistance is increased up until locking of the joint, in order to go automatically into a safe or secured state. The resistance may be increased continuously during the standing phase or when standing when there is increasing loading, the increase advantageously being carried out only whenever a threshold value, for example of the ground reaction force, is reached or exceeded. The ground reaction force may in this case be measured directly. In most cases, however, only a meaningful component of the ground reaction force, such as for example the component in the direction of, the lower leg, is measured. The initial resistance may be settable, so that the level from which the resistance is increased, and to which it is possibly reduced again, can be adapted to the patient.

In order to use the state of increased flexion resistance only whenever there is a risk of buckling of the knee joint, it is provided that the locking is only performed whenever the ground reaction force vector runs behind the knee axis, so that under further loading in the axial direction of the fitted leg an increasing bending would occur. Depending on the structure of the prosthesis or orthesis, this may take place at different bending angles. Particularly stably constructed joints, in which the ground reaction force vector lies well ahead of the joint axis in the stretched state, are only subjected to an increased resistance at a relatively great joint angle, while less stably constructed joints require an increased resistance already before that. A less stable and also less safe structure, for example due to a forward shifting of the knee joint, provides advantages for the patient if the buckling of the knee joint is prevented and the prosthesis is secured by the control. Under otherwise the same conditions, the forward shifting of the knee joint leads to quicker and greater knee bending when the heel strikes and dampens the impact. Furthermore, the hip-bending torque for initiating the swing phase and for bending the prosthesis in the swing phase decreases, which has a positive effect for the patient. The forward shifting of the knee joint also brings about a shortening of the length of the prosthesis in the mid-swing phase, which reduces the risk of the patient stumbling. Consequently, the resistance is also increased in dependence on the joint angle or the inertial angle of a joint component, in particular of the lower leg part and the upper leg part, since the ground reaction force vector can lie behind the knee joint axis even with a stretched knee joint and a stable structure when standing on a sloping level, which may lead to a buckling of the knee joint. The inertial angle is helpful especially to prevent locking during sitting, that is to say with an almost horizontal upper leg.

The resistance may also be increased or locked in dependence on the distance of the ground reaction force from a reference point on a connection part on the joint or in dependence on a torque about the reference point.

In order after increasing the resistance up to a lock to be able to use the joint device for activities other than standing, it is provided that the resistance is reduced, for example to the initial value, in dependence on an inertial angle, a changing of the inertial angle and/or the inertial angle velocity of a connection part of the joint. It is therefore detected that part of the joint is being moved, for example that the load on the prosthesis is being relieved or the user is rolling forward or backward by way of the prosthesis. It is detected from this that standing no longer applies, so that the resistance must be reduced.

Standing is the term used when the prosthetic foot is set down and the wearer of the prosthesis is not in a forward or backward movement. An axial load or ground reaction force is exerted on the prosthesis and the prosthetic foot. The prosthetic knee joint is usually stretched, although standing with a bent knee is also intended to be possible by the present method. This loading-dependent behavior is preferably implemented as a "function". A function can be given clearance or locked. If it is given clearance, it is always activated when the sensor criteria for increasing the resistance are satisfied. If the criteria are no longer satisfied, the joint can go over into other control states, such as for example a swing phase control. If it is locked, it can no longer be activated. The other control states are not affected by this however. It is, however, also possible to implement the control as a "mode".

The standing mode is a control behavior that has to be activated separately. Unlike a standing function, which exists permanently and enquires whether or not the criteria for the standing function are satisfied, to then perform a corresponding adaptation of the resistance or resistances, the mode, in the present method the standing mode, is activated by way of an activity to be carried out deliberately. If the method is implemented as a mode, the function of the joint is confined exclusively to the behavior described. The transition to other control states, such as for example a swing phase control, is only possible after deliberate deactivation of the mode.

It is likewise possible that, in spite of the presence of the corresponding ground reaction force and the joint angle, the increasing of the resistance is not initiated at all if there is an inertial velocity of a joint component, that is to say a standing state does not apply. The locking of the joint can likewise be ruled out in dependence on the inertial angle, for example if the upper leg part is inclined forward in the walking direction, that is to say the proximal end of the upper leg part lies ahead of the distal end of the upper leg part in the walking direction.

To determine the inertial angle of a connection part, it is possible to determine it directly or from the inertial angle of another connection part in conjunction with a corresponding joint angle.

When the joint is relieved of loading, for example when lifting the leg, a hysteresis may be provided, reducing the resistance again only when there is relatively low loading, that is to say that the threshold value must be fallen below significantly in order to bring about a reduction in resistance.

In order to reduce the resistance again when continuing to walk or sitting down, the inertial angle velocity of the connection part, the knee angle, the knee angle velocity, the changing of the distance of the ground reaction force from a connection part and/or the changing of the inertial angle of a connection part may be used. For example, the knee angle, the knee angle velocity and the inertial angle velocity are well suited for detecting forward walking. It is also provided that the locking of flexion is initiated whenever the knee angle velocity is zero or virtually zero, in order to ensure that the knee joint is only locked while at a standstill. This state may occur if the force vector lies behind the knee axis, but temporarily, until the flexion lock responds, the patient using the hip to compensate for the bending, so that the knee torque and the knee angle velocity become zero. When standing, the activated flexion lock may have the effect that the knee torque is bending, without the knee giving way.

The distance of the ground reaction force vector from a connection part is well suited for detecting sitting down. The reducing of the resistance may in this case be performed discretely or continuously when a threshold for the parameters mentioned is exceeded.

The reducing as well as the increasing of the resistance may be initiated by a number of parameters, for example loading, joint angle and inertial angle, there being various form functions by way of which it is determined by linking a number of conditions whether and by which factor the resistance is increased or reduced. This produces gentle locking and unlocking of the joint in dependence on a number of influencing variables.

Since a locking of the joint when sitting is sometimes undesired, for example to prevent a locked knee joint and a jamming joint when driving a car, it is provided that the resistance cannot be increased up to a lock if the upper leg part is almost horizontal. For this purpose, the inertial angle of the upper leg part is determined. The increase of the resistance up to a locking of the joint that is described above may be part of an overall control of a joint; it is also possible that it is the only function of a joint. It may in this case form a mode to be deliberately activated, which can be activated or deactivated by way of a setting device. It is likewise possible that this function is latently present, so that this function is present at all times in the normal control program of a knee joint during the standing phase or when standing if the preconditions for locking the joint are satisfied.

The device for carrying out the method, as it is described above, provides a settable resistance device, which is arranged between two components of an artificial orthotic or prosthetic joint that are arranged one against the other in a jointed manner and has a control device and sensors that detect information pertaining to the state of the device. Also provided is a setting device, by way of which the loading-dependent change in resistance can be activated and/or can be deactivated.

BRIEF DESCRIPTION OF THE DRAWINGS

An exemplary embodiment of the device is explained in more detail below on the basis of the accompanying figures, in which:

FIG. 1 shows a profile of the variation in resistance;

FIG. 2 shows criteria for controlling the change in resistance;

DETAILED DESCRIPTION

Figure 3:
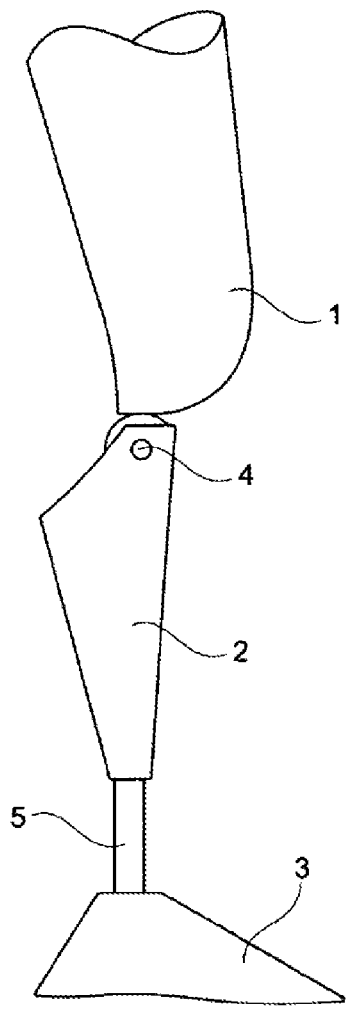
FIG. 3 shows a schematic representation of a prosthesis.

In FIG. 1, the variation in the resistance R or the change in resistance is shown against the loading due to the ground reaction force GRF. In the standing phase or while standing, the normal standing phase resistance $R_{stance}$ is set to obtain a gait pattern that is as natural as possible with a prosthesis or orthesis during walking. If a threshold value of the ground reaction force GRF is exceeded, the resistance R is raised, a continuous increasing of the resistance R up to a block resistance $R_{block}$ being achieved during the standing phase with increasing loading due to the ground reaction force GRF. This blocking resistance $R_{block}$ effectively prevents a flexion of the knee joint, but is advantageously dimensioned such that no mechanical damage occurs if a loading limit for individual components of the prosthesis or orthesis is exceeded. If in the further course of events the ground reaction force GRF is then reduced again, it is provided that the resistance is only reduced again from the blocking value $R_{block}$ when the loading has gone below the threshold value that was reached to initiate an increase in resistance. After falling below this threshold value, the resistance R is then reduced to the normal standing phase level until the standing phase resistance $R_{stance}$ is reached.

There are various ways in which the resistance to be set can be determined; in FIG. 2, form functions that can be used as factors for calculating the resistance R are represented. The curve on the right shows the function for the loading due to the ground reaction force GRF, which has been normalized. The curve on the left shows how further functions $f_N$ can be entered in the calculation of the setpoint resistance. Indicators for a movement of the joint, such as the knee angle velocity, the inertial angle velocity, the deviation of the distance of the ground reaction force of a joint part from the point in time of the lock coming into effect or the deviation of the inertial angle of a joint part before the lock comes into effect may serve as arguments for these functions. All of the functions $f_1$ to $f_N$ may be linked by multiplication to arrive at the setpoint value of the resistance, in that for example they weight the difference of a standing phase resistance from a blocking resistance and thus determine by which amount the standing phase resistance $R_{stance}$ is increased. The maximum value for the blocking resistance $R_{block}$ reduced by the value for the normal standing phase resistance $R_{stance}$ is multiplied by the two arguments $f_1$ and $f_N$. If a function is zero, the standing phase resistance $R_{stance}$ remains unchanged; as soon as all of the functions $f_1$ to $f_N$ are greater than 0, the standing phase resistance $R_{stance}$ is increased or, if the functions become smaller, the increased resistance is reduced. The resistance R is therefore calculated from $$R = R_{stance} + (R_{block} - R_{stance}) * f_1(ARG_1) * f_2(ARG_2) * \ldots + f_N(ARG_N)$$

After reducing the resistance following activation of the block, a set of functions $f_N$ that is different from that used for activating the lock may be used.

In FIG. 3, a schematic representation of a leg prosthesis with an upper leg shaft 1 for receiving an upper leg stump is shown. The upper leg shaft 1 is also referred to as the upper connection part. Arranged on the upper connection part 1 is a lower connection part 2 in the form of a lower leg shaft with a resistance device. Arranged on the lower connection part 2 is a prosthetic foot 3. The lower connection part 2 is pivotably fastened to the upper connection part 1 by way of a joint 4. Arranged in the joint 4 is a torque sensor, which determines the effective knee torque. Provided in the lower connection part 2 is a connecting part 5 to the prosthetic foot 3, in which a device for determining the effective axial force and the ankle torque is accommodated. It is possible that not all the sensors are present in a leg prosthesis; there may perhaps be no need for an ankle torque sensor or the knee torque sensor.

Apart from the resistance device, which offers the bending and stretching resistance, in the lower connection part 2 there is a control device, by way of which it is possible to change the respective resistance on the basis of the received sensor data and the evaluation of the sensor data, in that an actuator is activated in a way corresponding to the evaluation and the resistance device is set such that there is the desired or required resistance in the direction of extension and/or flexion. For this purpose, it may be provided that the sensor data are used for producing at least one auxiliary variable, which is obtained by way of a mathematical linking of two or more sensor data. This makes it possible for a number of force or torque sensors to be linked to one another to calculate forces, distances and/or torques that are not acting directly in the region of the sensors. For example, it is possible to calculate stress resultants, average torques or distances in specific reference planes, in order on this basis to be able to assess which functions must be performed at the time in question in order that a gait pattern that is as natural as possible can be achieved. Referred to here as a function are those control sequences that occur in the course of a natural movement, whereas a mode is a control state that is set by an arbitrary act, for example by actuating a separate switch or by a deliberate, possibly deliberately unnatural, sequence of movements.

Figure 4:
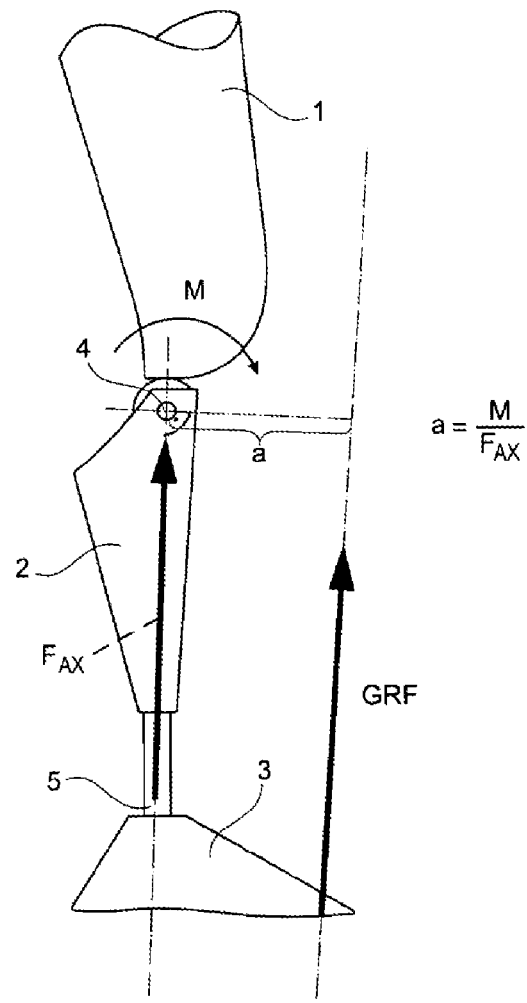
FIG. 4 shows a schematic representation for the calculation of a distance.

In FIG. 4, it is schematically represented how the distance a of the ground reaction force vector GRF from the knee axis is used as an argument. The distance a is calculated from the quotient of the knee torque M and the axial force $F_{AX}$. The greater the knee torque M is in relation to the axial force $F_{AX}$, the greater the distance a of the ground reaction force vector GRF at the reference height, which in the present case forms the knee axis. On the basis of the argument a, it is possible to vary the stretching resistance and/or the bending resistance, since this argument a can be used to calculate whether standing applies or standing has been discontinued, so that on this basis a predetermined bending and/or stretching resistance is set. It can be determined by changing the argument a how the movement at the time in question is proceeding, so that an adaptation of the stretching and/or bending resistance can take place within the movement, including within the standing phase or the swing phase. The changing of the resistances preferably takes place continuously and in dependence on the changing of the argument or the arguments.

Figure 5:
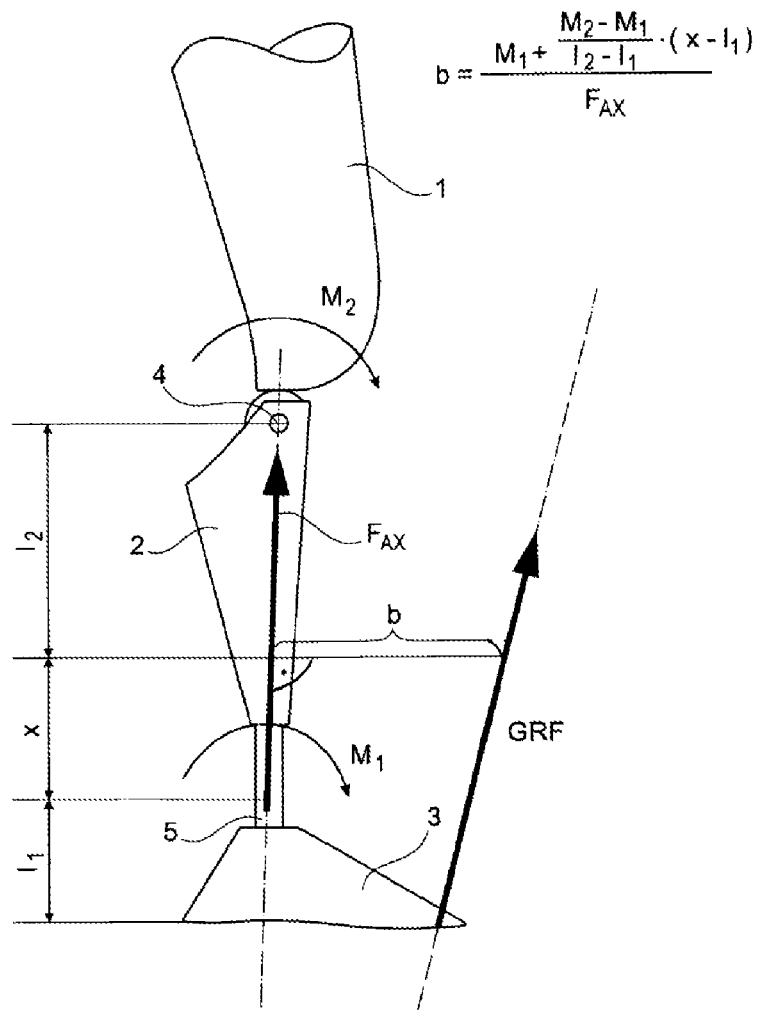
FIG. 5 shows a schematic representation for the calculation of a distance on the basis of a number of sensor values.

In FIG. 5 it is shown how the argument b in the form of the distance of the ground reaction force vector GRF at a reference height from the connecting line of the torque sensors can be calculated. The argument b is calculated from $$b = \frac{M1 + \frac{M2-M1}{l2-l1} * (x-l1)}{FAX}$$

where $M_1$ is the effective torque in the connecting part 5, generally the ankle torque at the height $l_1$ from the floor, the torque $M_2$ is the knee torque at the height of the knee axis 4, which lies at a distance of $l_2$ from the floor. The variable x is the reference height, the force $F_{AX}$ is the effective axial force within the connecting part 5 or in the lower connection part 2. By changing the argument b, it is possible, as prescribed, to set the respective resistances and adjust them to the given changes continuously, both during the swing phase and during the standing phase. This makes it possible to activate various functions, which are automatically detected, for example a standing function that is used for example to prevent the knee joint from bending unwantedly.

The increasing of the resistance, in particular the flexion resistance, during the standing phase or while standing may be implemented as a latent function that is constantly available. If the patient is in the standing phase or standing, the resistance to a flexion is automatically increased until the blocking of the joint, in particular the knee joint. The knee angle is also taken into consideration here. If, for example, the knee is in a stretched position, no locking of the flexion movement is necessary on account of the generally stable structure. If, however, the knee joint is in a slightly bent position, for example greater than 4° between the longitudinal extent of the lower leg part and the upper leg part, and if then there is also loading from a ground reaction force, the knee joint is then automatically locked, since it must be assumed that, in spite of the bending of the knee, no flexion is desired.

Figure 6:
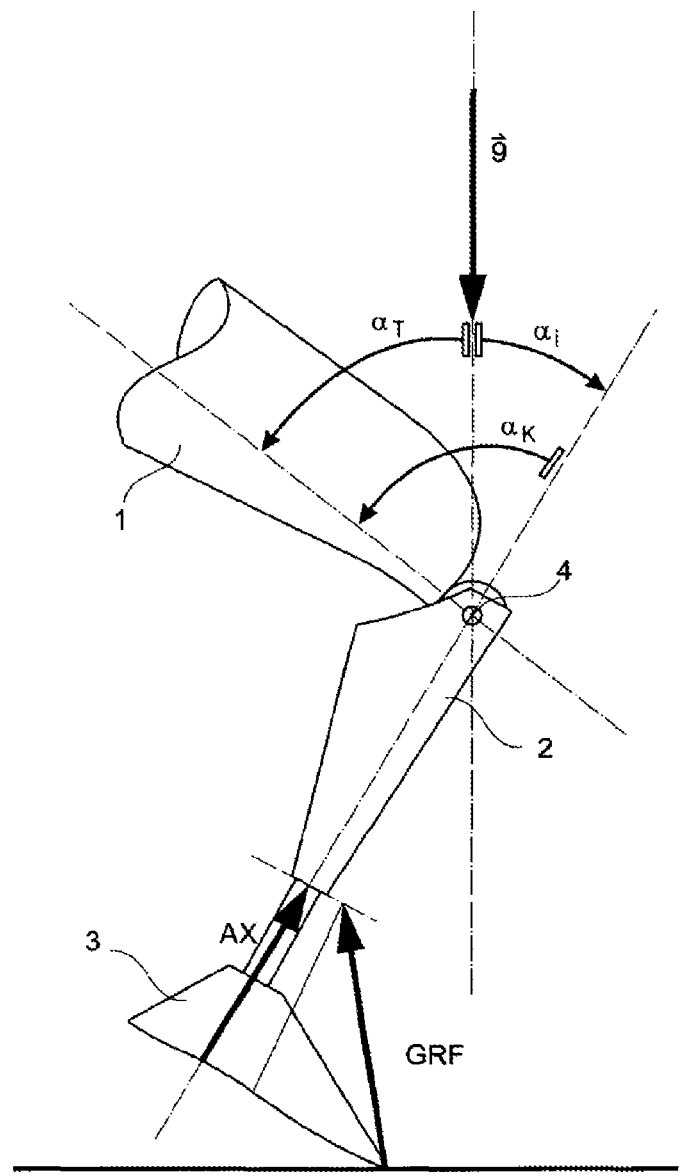
FIG. 6 shows a convention of the angle indications.

In FIG. 6, the prosthesis is schematically represented in a sitting position. If the user of the prosthesis is in a sitting position, it is comfortable if the extension resistance and the flexion resistance of the resistance device are low, so that the movements performed during sitting, which generally have a small extent of movement, can be carried out unimpaired.

To be able to carry out the changes in resistance and a determination of the state automatically, it is provided that the inertial angle $\alpha_T$ and/or the knee angle $\alpha_K$ are measured. The inertial angle $\alpha_T$ of the upper leg part 1 is measured in relation to the vertical, which is assumed to be acting in the direction of gravitational force. In FIG. 6, this is indicated by the gravitational force vector g. Assumed as the reference variable for the inertial angle $\alpha_T$ is the longitudinal axis of the upper leg part 1, which passes through the pivoting axis of the prosthetic knee joint 4. In this case, the longitudinal axis corresponds approximately to the orientation of a natural upper leg bone and extends substantially centrally in relation to the upper leg part 1, which is generally formed as an upper leg shaft.

The knee angle $\alpha_K$ lies between the longitudinal extent of the lower leg part 2 and the longitudinal extent of the upper leg part 1. Here, too, the longitudinal extent of the lower leg part 2 passes through the joint axis of the prosthetic knee joint 4. The knee angle $\alpha_K$ can be calculated from the inertial angle $\alpha_T$ of the upper leg part 1 and the inertial angle $\alpha_i$ of the lower leg part 2, an adapted sign convention being introduced on account of the calculation of the inertial angles $\alpha_T$ and $\alpha_i$ on the basis of the gravitational force vector g, so that the inertial angle $\alpha_T$ of the upper leg part is obtained from the difference between the knee angle $\alpha_K$ and the inertial angle $\alpha_i$ of the lower leg part 2.

In addition, the ground reaction force GRF or the axial force AX that is effective in the longitudinal direction of the lower leg part 2 is determined, in order to decide on the basis of the forces present whether the user of the prosthesis is in a sitting or standing position.

The ground reaction force GRF is generally reduced significantly when the user of the prosthesis is sitting. If, therefore, the ground reaction force GRF falls below a threshold value, this is a factor in the assessment as to whether a sitting state applies. If a great ground reaction force GRF is detected, a standing position can be assumed, similarly standing up can be assumed; in both cases, it is appropriate for the flexion resistance to be increased in order to avoid unwanted collapsing or buckling under a high ground reaction force GRF.

An abrupt increasing of the resistance after reaching specific threshold values is often found to be uncomfortable. It is therefore provided that, after reaching a threshold value for the ground reaction force GRF, the resistance is continuously increased. Typically, the increasing of the resistance would be carried out between 20% and 3% of the bodyweight, the reduction between 20% and 10% of the bodyweight. If, however, there is too great a knee angle $\alpha_K$ or inertial angle $\alpha_T$ or if the joint 4 is moved, it can be assumed that a standing situation does not apply, so that a reduction of the resistance can be performed, possibly to an initial resistance. If the upper leg part 1 is in an inclined position, that is to say in a substantially horizontal state, so that the inertial angle $\alpha_T$ is between for example 70° and 110°, it is intended that increasing the resistance should be ruled out. It may even possibly be that, after a predetermined time has elapsed, a reduction of the resistance of the resistance device to below the standing phase resistance may be performed, since it can then be assumed that the user of the prosthesis is sitting.

For determining the inertial angle velocity, the changing of the inertial angle $\alpha_1$ over time is determined, so as to obtain an angle velocity $\overline{\omega}_1$ that can be determined in terms of the amount and direction. So if there is a specific inertial angle $\alpha_1$ and a specific inertial angle velocity $\overline{\omega}_1$, it can be assumed that there is a movement situation, that is to say not a standing situation in which locking or blocking of the knee joint would have to be performed.

In the case of the present method, it is provided that, immediately after loading that exceeds a specific threshold value, a lock comes into effect without any time delay, so that no separate activation of an increase in resistance has to be initiated by special movements that do not correspond to a normal sequence of movements. A loading signal that represents the magnitude of the loading is provided by way of the ground reaction force GRF, the ground reaction force GRF being sufficient to activate the standing function. Further variables such as torques or inertial angles may be used additionally, that is to say to verify the decision as to whether a standing state or a standing phase actually applies. With the claimed method it is possible to lock the knee or some other joint in the bent position or under bending forces, the locking advantageously only coming into effect when there is a slightly bent knee, for example as from a knee bending of 4° as the knee angle.

The invention claimed is:

1. A method for controlling an orthotic or prosthetic joint of a lower extremity with a resistance device, which is assigned at least one actuator by way of which at least one of a bending and stretching resistance is changed in dependence on sensor data, information pertaining to a state of the joint being provided by way of sensors during use of the joint, wherein during a standing phase or when standing, the resistance is increased from an initial value up until a locking of the joint in dependence on a measured ground reaction force, and after the resistance is increased, reducing the resistance in dependence on an inertial angle of a connection part of the joint.

2. The method as claimed in claim 1, wherein the resistance is increased continuously during the standing phase when there is increasing loading.

3. The method as claimed in claim 1, wherein the resistance is increased when a threshold value is reached or exceeded.

4. The method as claimed in claim 1, wherein the resistance is increased in dependence on at least one of a joint angle and the inertial angle of the connection part of the joint.

5. The method as claimed in claim 1, wherein the resistance is increased or locked in dependence on a distance of the ground reaction force from a reference point on the connection part of the joint or in dependence on a torque about the reference point.

6. The method as claimed in claim 1, wherein after increasing the resistance, the resistance is reduced in dependence on at least one of the inertial angle, a changing of the inertial angle, and an inertial angle velocity of the connection part of the joint.

7. The method as claimed in claim 1, wherein the inertial angle of the connection part is determined directly or from the inertial angle of another connection part and a joint angle.

8. The method as claimed in claim 1, wherein after the increasing, the resistance is reduced in dependence on at least one of a measured joint angle and a measured joint angle velocity.

9. The method as claimed in claim 1, wherein after the increasing, the resistance is reduced again to the initial value in dependence on at least one of a distance and the changing of the distance of the ground reaction force from a reference point on the connection part of the joint.

10. The method as claimed in claim 1, wherein the criteria for at least one of increasing and reducing the resistance are combined with one another directly in a characteristic diagram.

11. The method as claimed in claim 1, wherein there are a number of control algorithms, which operate on the basis of measured values of different devices for detecting angles and forces, so that, in the case of failure of one device for detecting angles and forces, the other measured values are used for controlling the changing of the stretching and/or bending resistance.

12. A device for carrying out the method as claimed in claim 1, comprising a settable resistance device, which is arranged between two components of an artificial orthotic or prosthetic joint that are arranged one against the other in a jointed manner, with a control device and sensors that detect information pertaining to the state of the device, wherein a setting device is provided and a loading-dependent change in resistance can be activated or can be deactivated by way of the setting device.

13. A method for controlling an orthotic or prosthetic joint of a lower extremity, comprising:
   providing a resistance device, at least one actuator, and a plurality of sensors;
   changing at least one of a bending resistance and a stretching resistance in the joint based on sensor data provided by the plurality of sensors;
   providing information from the plurality of sensors related to a state of the joint during use of the joint;
   increasing the at least one of the bending resistance and the stretching resistance from an initial value up to a locking of the joint in a standing phase or when standing based on a measured ground reaction force;

wherein after increasing the at least one of the bending resistance and the stretching resistance, reducing the at least one of the bending resistance and the stretching resistance based on an inertial angle of a connection part of the joint.

14. The method as claimed in claim 13, wherein the at least one of the bending resistance and the stretching resistance is increased continuously during the standing phase when there is increasing loading of the joint.

15. The method as claimed in claim 13, wherein the at least one of the bending resistance and the stretching resistance is increased when a threshold value is reached or exceeded.

16. The method as claimed in claim 13, wherein the at least one of the bending resistance and the stretching resistance is increased based on at least one of a joint angle and the inertial angle of the connection part.

17. The method as claimed in claim 13, wherein the at least one of the bending resistance and the stretching resistance is increased or locked based on a distance of the ground reaction force from a reference point on the connection part of the joint or based on a torque about the reference point.

18. The method as claimed in claim 13, wherein the at least one of the bending resistance and the stretching resistance is reduced based on at least one of the inertial angle, a changing of the inertial angle, and an inertial angle velocity of the connection part of the joint.

19. The method as claimed in claim 18, wherein the inertial angle of the connection part is determined directly or from an inertial angle of another connection part and a joint angle.

20. The method as claimed in claim 13, wherein after increasing the at least one of the bending resistance and the stretching resistance, reducing the at least one of the bending resistance and the stretching resistance based at least in part on a measured joint angle and a measured joint angle velocity.

* * * * *